US009525250B2

(12) United States Patent
De Jong et al.

(10) Patent No.: US 9,525,250 B2
(45) Date of Patent: *Dec. 20, 2016

(54) LASER DIRECT STRUCTURED CONNECTION FOR INTRAVASCULAR DEVICE

(71) Applicant: VOLCANO CORPORATION, San Diego, CA (US)

(72) Inventors: Duane De Jong, Elk Grove, CA (US); Douglas Meyer, Folsom, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/988,424

(22) Filed: Jan. 5, 2016

(65) Prior Publication Data

US 2016/0134068 A1      May 12, 2016

Related U.S. Application Data

(63) Continuation of application No. 14/107,744, filed on Dec. 16, 2013, now Pat. No. 9,226,711.

(60) Provisional application No. 61/740,568, filed on Dec. 21, 2012.

(51) Int. Cl.
*H01R 24/58* (2011.01)
*A61B 5/00* (2006.01)
*A61B 8/12* (2006.01)

(52) U.S. Cl.
CPC ............. *H01R 24/58* (2013.01); *A61B 5/6852* (2013.01); *A61B 8/12* (2013.01); *A61B 2562/227* (2013.01); *H01R 2201/12* (2013.01); *Y10T 29/49204* (2015.01)

(58) Field of Classification Search
CPC .. H01R 24/58; H01R 2103/00; H01R 2107/00
USPC .................................................. 439/668, 669
See application file for complete search history.

(56) References Cited

U.S. PATENT DOCUMENTS

| 5,176,141 A | 1/1993 | Bom et al. |
| 5,651,366 A | 7/1997 | Liang et al. |
| 5,771,895 A | 6/1998 | Slager |
| 6,134,003 A | 10/2000 | Tearney et al. |
| 6,421,164 B2 | 7/2002 | Tearney et al. |
| 6,592,520 B1 * | 7/2003 | Peszynski ................ A61B 8/12 600/437 |
| 6,673,015 B1 | 1/2004 | Glover et al. |
| 6,696,173 B1 | 2/2004 | Naundorf et al. |
| 7,060,421 B2 | 6/2006 | Naundorf et al. |
| 7,358,921 B2 | 4/2008 | Snyder et al. |
| RE40,608 E | 12/2008 | Glover et al. |
| 7,594,828 B2 * | 9/2009 | Alexander ............... A61N 1/05 439/669 |

(Continued)

*Primary Examiner* — Chandrika Prasad
*Assistant Examiner* — Harshad Patel
(74) *Attorney, Agent, or Firm* — Haynes and Boone, LLP

(57) ABSTRACT

The invention generally relates to intravascular imaging catheters and methods of making catheters for imaging systems. The invention provides a connector for an imaging catheter that includes a unitary body with very thin electrical contacts that are formed on the surface of the body. Due to the scale of the contacts, the connector operates essentially as a single unitary piece of material. Each of the leads may be less than about 100 μm wide and less than about 8 μm thick, and further the leads may be spaced apart by less than about 160 μm.

20 Claims, 7 Drawing Sheets

(56) References Cited

U.S. PATENT DOCUMENTS

| | | | |
|---|---|---|---|
| 7,632,753 B1* | 12/2009 | Rusli | H01L 21/76804 257/698 |
| 7,783,337 B2 | 8/2010 | Feldman et al. | |
| 7,787,127 B2 | 8/2010 | Galle et al. | |
| 7,846,101 B2 | 12/2010 | Eberle et al. | |
| 7,995,210 B2 | 8/2011 | Tearney et al. | |
| 7,999,938 B2 | 8/2011 | Wang | |
| 2004/0015065 A1 | 1/2004 | Panescu et al. | |
| 2004/0248439 A1 | 12/2004 | Gernhardt et al. | |
| 2004/0260355 A1* | 12/2004 | Holleman | A61N 1/3752 607/37 |
| 2007/0207186 A1* | 9/2007 | Scanlon | A61F 2/07 424/424 |
| 2008/0180683 A1 | 7/2008 | Kemp | |
| 2008/0291463 A1 | 11/2008 | Milner et al. | |
| 2009/0043191 A1 | 2/2009 | Castella et al. | |
| 2009/0292048 A1 | 11/2009 | Li et al. | |
| 2010/0220334 A1 | 9/2010 | Condit et al. | |
| 2011/0152771 A1 | 6/2011 | Milner et al. | |
| 2011/0223812 A1* | 9/2011 | Prest | H01R 13/035 439/669 |
| 2012/0095340 A1 | 4/2012 | Smith | |
| 2012/0232400 A1 | 9/2012 | Dickinson et al. | |
| 2012/0265077 A1 | 10/2012 | Gille et al. | |
| 2012/0271170 A1 | 10/2012 | Emelianov et al. | |
| 2012/0276390 A1 | 11/2012 | Ji et al. | |
| 2012/0279764 A1 | 11/2012 | Jiang et al. | |

* cited by examiner

LASER DIRECT STRUCTURED CONNECTION FOR INTRAVASCULAR DEVICE

CROSS REFERENCE TO RELATED APPLICATIONS

This Application is a continuation of U.S. Ser. No. 14/107,744 filed on Dec. 16, 2013 which claims priority to and the benefit of U.S. Provisional Patent Application No. 61/740,568, filed on Dec. 21, 2012, each of which is hereby incorporated by reference in its entirety.

FIELD OF THE INVENTION

The invention generally relates to intravascular imaging catheters and methods of connecting catheters to imaging systems.

BACKGROUND

Over a person's life, plaque builds up in their arteries in a condition sometimes known as hardened arteries. The accumulation of plaque can pose a serious threat of a stroke or heart attack, even in cases in which no symptoms emerge and the person lives unawares of the threat. To help identify people that are at risk of a stroke or heart attack, doctors use imaging systems to look inside of a patient's blood vessels and study the plaque.

Typical intravascular imaging systems, such as intravascular ultrasound (IVUS) systems, include a long, thin catheter that is connected to a computer-controlled imaging system. The doctor inserts the catheter into the patient's blood vessels and the tip of the catheter takes a picture from within the blood vessel. The picture can be displayed on a monitor so that the doctor can see and examine any plaque buildup.

It is common for the catheter to be a single-use, disposable part and for the imaging system to include a control station, computer, monitor and other components. Each imaging operation requires a doctor to scrub in, unwrap a new catheter, connect it to the system, and perform the imaging operation. Since the image is transferred from the catheter into the computer in the form of electrical signals, each catheter must make a reliable electrical contact with the system. Unfortunately, existing imaging catheters have fragile connection mechanisms.

In the existing catheters, the signal wires are connected to metal rings that are spaced apart by a number of plastic slugs and all of the parts are mounted as an assemblage along a central core. Not only are these connectors difficult and expensive to make, they can fall apart if misassembled or mishandled. Additionally, it has been observed that the structure of existing catheters is associated with misuse. Sometimes they, are not inserted properly, and the necessary electrical contacts are not made. Since existing catheters do not always provide satisfactory results, imaging operations can require do-overs—the catheter is withdrawn and discarded and a new one is used. This increases the cost, complexity, and risk of complications in intravascular imaging procedures. Also, the scale of the components used in existing catheters places a limit on the image information that can be electrically transmitted into the computer system. Since only a few electrical contacts can be disposed along the mating portion of existing catheter connectors, it is difficult to incorporate new functionality into the imaging transducers, as there is not room at the connection jacks to add more connection points.

SUMMARY

The invention provides a connector for an imaging device such as an imaging catheter or guidewire that includes a unitary body with very thin electrical contacts that are formed on the surface of the body. Due to the micron-scale thinness of the contacts, the connector operates essentially as a single unitary piece of material. Since the connector is not an assemblage of pieces, it cannot be misassembled nor does it fall apart. Additionally, connectors of the invention can be manufactured with uniformity, providing a product that are used consistently and correctly. Due to the uniformity of the connectors, doctors will find it easier to make a good connection for each and every imaging operation. This will allow imaging operations to proceed successfully using the first catheter that is installed. Moreover, the electrical contacts, and the leads that conduct electricity to those contacts, can be provided at a very fine scale. For example, the width of ten independent leads running alongside one another can be less than a few millimeters. Due to the scale of the electrical contacts and leads, an intravascular imaging device can carry a greater number of imaging signals from the patient into the computer system. This allows new technologies to be incorporated into existing imaging catheters or guidewires, and provides for multi-function systems that operate via a single catheter or guidewire to perform diverse imaging functions with a single insertion procedure. Since devices of the invention are used more reliably to provide intravascular images with fewer failures and do-overs, intravascular imaging services can reach a greater number of patients while also being safer and more affordable. Since new imaging technologies can be deployed alongside other imaging technologies, intravascular imaging can provide more information at a finer scale about conditions within a patient's arteries. This allows, for example, accumulations of plaque to be detected in more people and at critical early stages, giving doctors the information they need to plan for their patients' health.

In certain aspects, the invention provides a connector device for a medical imaging device that has an extended body made with a thermoplastic doped with an organo-metal complex. The body has a conductive contact disposed on a surface of the proximal end and a conductive lead extending along a length of the body and in electrical contact with the conductive contact. The conductive contact may be less than about 10 μm thick. In some embodiments, the conductive lead is a metal trace on a surface of the body that is less than about 150 μm wide and less than about 10 μm thick. An end of the body may be substantially cylindrical, with the contacts on the outer surface. For example, each contact may define a ring extending around the cylindrical member. For a female connector, the end substantially defines a cylindrical hollow and the conductive contact is on an inner surface of the cylindrical hollow, e.g., as a ring extending around an inside surface of the cylindrical hollow. In certain embodiments, the device has a plurality of conductive contacts disposed on the surface of the proximal end and each in electrical contact with one of a plurality of conductive leads extending along a length of the body. The device may be provided in a male form factor plug configured so that if inserted into a corresponding jack the plug may be rotated with respect to the jack while maintaining constant electrical contact from each of the conductive leads to corresponding conductors in the jack. The connector device may be on an intravascular imaging catheter. It may further include a plurality of conductive leads extending along the length of the body, wherein each of the leads are less than about 150 µm wide and less than about 10 µm thick, and further wherein the plurality of leads are spaced apart by less than about 200 µm (e.g., each of the leads may be less than about 100 µm wide and less than about 8 µm thick, and further the leads may be spaced apart by less than about 160 µm). In some embodiments, the conductive contact is less than about 5 µm thick and the conductive lead is disposed on a surface of the body and is less than about 5 µm thick, or even less than about 3 µm thick with the conductive lead being less than about 3 µm thick.

In related aspects, the invention provides a method of making a connector method for a medical imaging catheter by molding a thermoplastic doped with an metal-organic complex into an extended body having a proximal end and a distal end; irradiating an area of a surface of the body with a laser to make a metal from the metal-organic complex available at the surface; and depositing a conductor metal on the area to provide a conductive contact at the proximal end. The metal may be deposited by an electroless process and may provide a layer no greater than about 10 µm thick. Methods of the invention include attaching the body to an ultrasonic imaging device and providing an electrical connection between the conductive lead and a piezoelectric transducer in the imaging device. The connector and catheter may include a plurality of conductive contacts disposed on the surface of the proximal end and each in electrical contact with one of a plurality of conductive leads extending to the transducer. In some embodiments, the catheter terminates in a male form factor plug so that if inserted into a corresponding jack the plug may be rotated with respect to the jack while maintaining constant electrical contact from each of the conductive leads to corresponding conductors in the jack.

DETAILED DESCRIPTION

The invention provides systems and methods by which an electroless plating process can be employed to fashion a catheter connection structure with a body of thermoplastic having a thin conductive contact on a surface thereof.

Figure 1:
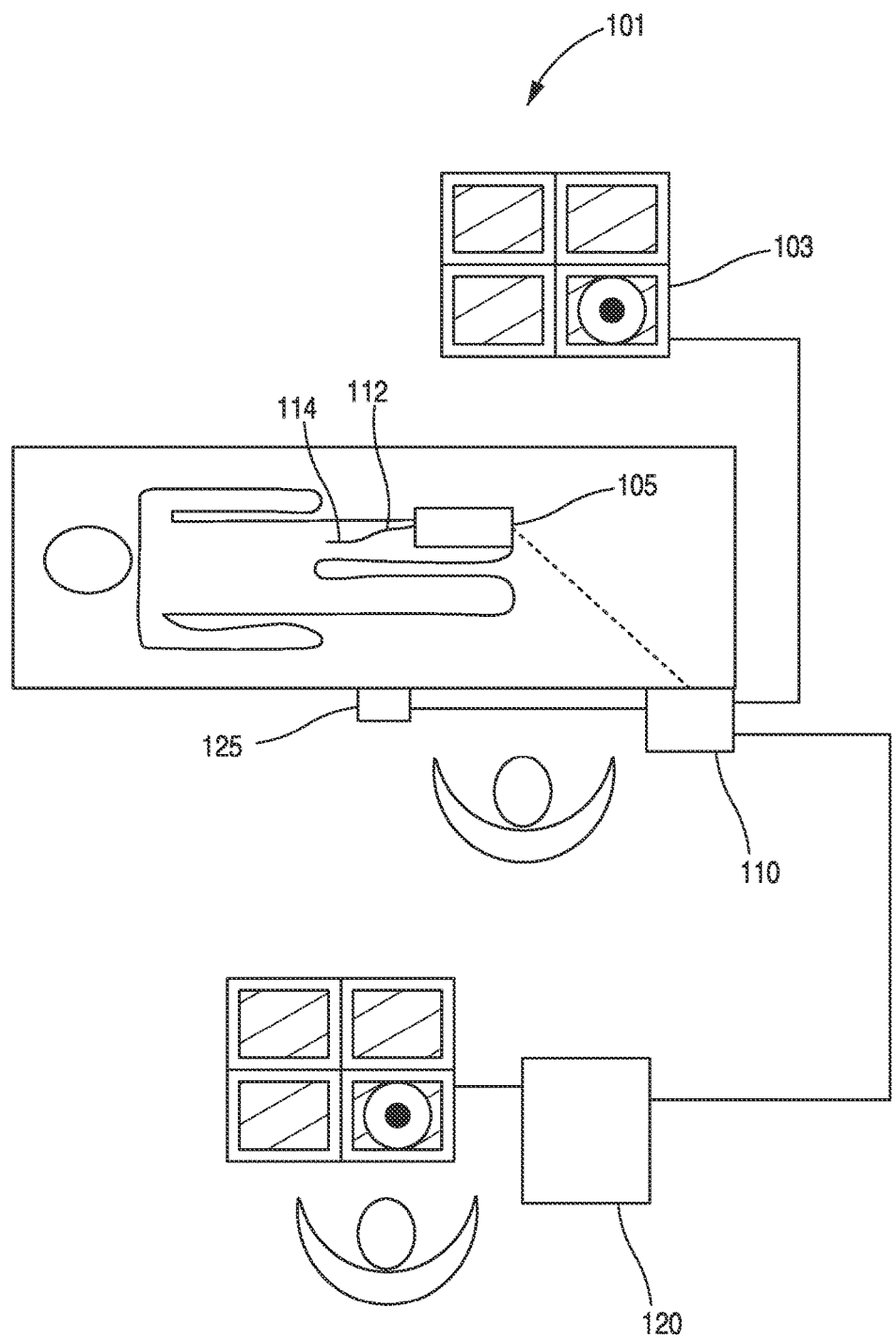
FIG. 1 shows an imaging system for catheter-based imaging.

FIG. 1 diagrams an imaging system 101 that includes a computer unit 120 connected to a control station 110 and including an optional navigational device 125, such as a joystick or similar. System 101 further may include a patient interface module (PM) 105 operably connected to control station 110 or computer unit 120 and an imaging catheter 112 extends from PIM 105. Imaging catheter 112 my generally include a imaging device 114 at a distal end, to be used for collecting an intravascular image of a patient's tissue, which image can be displayed, for example, on monitor 103.

System 101 is operable for use during diagnostic imaging of the peripheral and coronary vasculature of the patient. System 101 can be configured to automatically visualize boundary features, perform spectral analysis of vascular features, provide qualitative or quantitate blood flow data, or a combination thereof.

In some embodiments, system 1011 is used for intravascular ultrasound (IVUS) imaging. For IVUS, system 101 employs a sterile, single use intravascular ultrasound imaging catheter 112. Catheter 112 is inserted into the coronary arteries and vessels of the peripheral vasculature under the guidance of angiogrpahic system 107. System 101 may be integrated into existing and newly installed catheter laboratories (angiography suites.) The system configuration is flexible in order to fit into the existing catheter laboratory work flow and environment. For example, the system can include industry standard input/output interfaces for hardware such as navigation device 1125, which can be a bedside mounted joystick. System 101 can include interfaces for one or more of an EKG system, exam room monitor, bedside rail mounted monitor, ceiling mounted exam room monitor, and server room computer hardware. System 101 connects to catheter 112 via PIM 105, which may contain a type CF (intended for direct cardiac application) defibrillator proof isolation boundary.

Figures 2, 3:
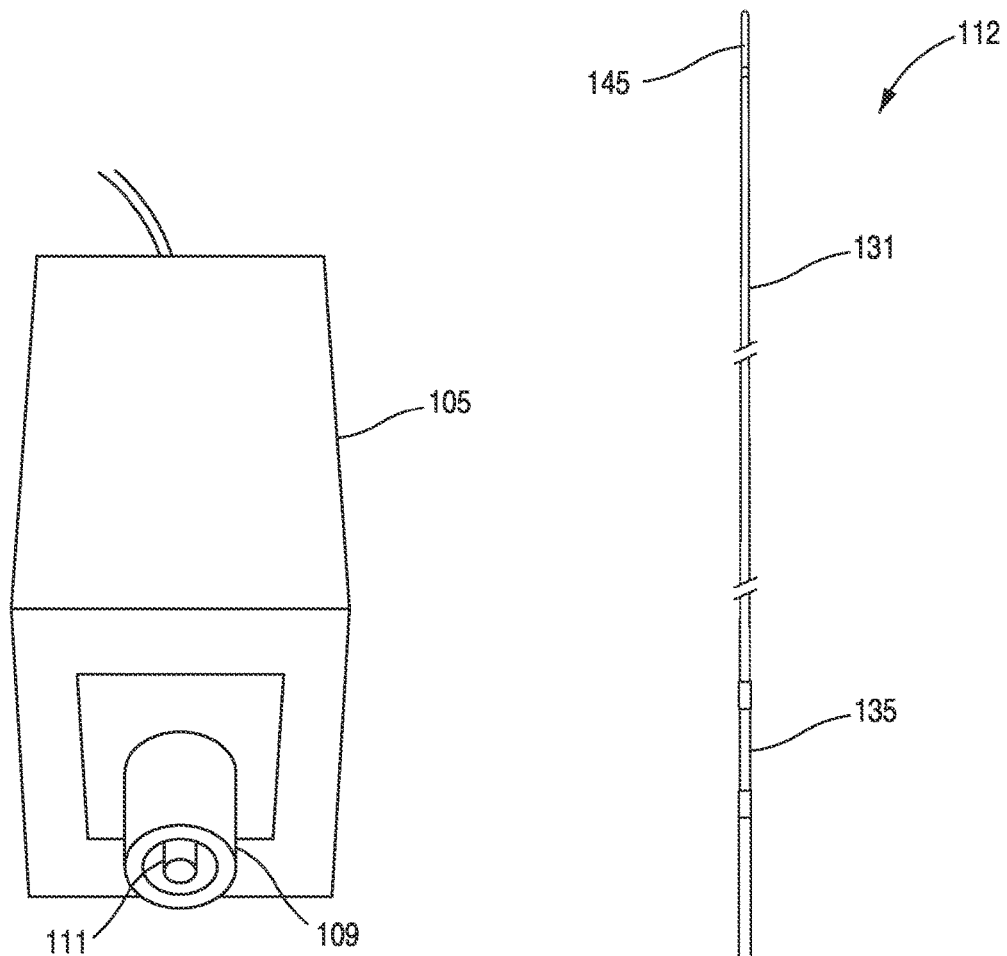
FIG. 2 depicts an interface module of an imaging system.
FIG. 3 shows a catheter of an imaging system.

FIG. 2 depicts a PIM 105 according to certain embodiments of the invention. PIM 105 includes connection port 109, here depicted as having a male connector 111 disposed therein available for connection to catheter 112. In an alternative embodiment, discussed below, catheter 112 includes male connector 111 and PIM 105 connection port 109 is dimensioned to couple with male connector 1111 on catheter 112. In IVUS, electrical signals are sent from PIM 105 to excite a piezoelectric transducer at the imaging unit 114 of catheter 112. Those electrical signals require electrical leads along a length of catheter 112 and a corresponding set of electrical contacts on the connection surfaces of connection port 109 and catheter 112. IVUS systems are discussed in U.S. Pat. No. 6,673,015; U.S. Pub. 2012/0265077; and U.S. R640,608 E, while catheters are described in U.S. Pat. No. 7,846,101; U.S. Pat. No. 5,771,895; U.S. Pat. No. 5,651,366; U.S. Pat. No. 5,176,141; U.S. Pub. 2012/0271170; U.S. Pub. 2012/0232400; U.S. Pub. 2012/0095340; U.S. Pub. 2009/0043191; U.S. Pub. 2004/0015065, the contents of which are incorporated by reference herein in their entirety for all purposes.

FIG. 3 shows a catheter 112 according to certain embodiments of the invention. As shown in FIG. 3, catheter 112 includes an extended body 135 with a distal portion 131 and a proximal portion 137. A piezoelectric transducer 145 is disposed at the distal portion 131. Proximal portion 137 terminates at connection member 141. To carry the aforementioned electrical signals, connection member 141 includes one or more electrical contact points, discussed in greater detail below.

All other input/output interfaces within the patient environment may utilize both primary and secondary protective earth connections to limit enclosure leakage currents. The primary protective earth connection for controller 125 and control station 110 can be provided through the bedside rail mount. A secondary connection may be via a safety ground wire directly to the bedside protective earth system. Monitor 103 and an EKG interface can utilize the existing protective earth connections of the monitor and EKG system and a secondary protective earth connection from the bedside protective earth bus to the main chassis potential equalization post.

Computer device 120 can include a high performance dual Xeon based system using an operating system such as Windows XP professional. Computer device 120 may be configured to perform real time intravascular ultrasound imaging while simultaneously running a tissue classification algorithm referred to as virtual histology (VH). The application software can include a DICOM3 compliant interface, a work list client interface, interfaces for connection to angiographic systems, or a combination thereof. Computer device 120 may be located in a separate control room, the exam room, or in an equipment room and may be coupled to one or more of a custom control station, a second control station, a joystick controller, a PS2 keyboard with touchpad, a mouse, or any other computer control device.

Computer device 120 may generally include one or more USB or similar interfaces for connecting peripheral equipment. Available USB devices for connection include the custom control stations, the joystick, and a color printer. In some embodiments, control system includes one or more of a USB 2.0 high speed interface, a 50/100/1000 baseT Ethernet network interface, AC power input, PS2 jack, Potential Equalization Post, 1 GigE Ethernet interface, microphone and line inputs, line output VGA Video, DVI Video interface, PIM interface, ECG interface, other connections, or a combination thereof. As shown in FIG. 1, computer device 120 is generally linked to control station 110. Control station 110 may be provided by any suitable device, such as a computer terminal (e.g., on a kiosk). In some embodiments, control system 110 is a purpose built device with a custom form factor.

In certain embodiments, systems and methods of the invention include processing hardware configured to interact with more than one different three dimensional imaging system so that the tissue imaging devices and methods described here in can be alternatively used with OCT, IVUS, or other hardware.

Any target can be imaged by methods and systems of the invention including, for example, bodily tissue. In certain embodiments, systems and methods of the invention image within a lumen of tissue. Various lumen of biological structures may be imaged including, but not limited to, blood vessels, vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

In certain embodiments, system 101 is used for optical coherence tomography (OCT) imaging. OCT is used in interventional cardiology, for example, to help diagnose coronary artery disease. OCT systems and methods are described in U.S. Pub. 2011/0152771; U.S. Pub. 2010/0220334; U.S. Pub. 2009/0043191; U.S. Pub. 2008/0291463; and U.S. Pub. 2008/0180683, the contents of each of which are hereby incorporated by reference in their entirety.

In OCT, a light source delivers a beam of light to an imaging device to image target tissue. Within the light source is an optical amplifier and a tunable filter that allows a user to select a wavelength of light to be amplified. Wavelengths commonly used in medical applications include near-infrared light, for example between about 800 nm and about 1700 nm.

Generally, there are two types of OCT systems, common beam path systems and differential beam path systems, that differ from each other based upon the optical layout of the systems. A common beam path system sends all produced light through a single optical fiber to generate a reference signal and a sample signal whereas a differential beam path system splits the produced light such that a portion of the light is directed to the sample and the other portion is directed to a reference surface. Common beam path interferometers are further described for example in U.S. Pat. No. 7,999,938; U.S. Pat. No. 7,995,210; and U.S. Pat. No. 7,787,127, the contents of each of which are incorporated by reference herein in its entirety.

In a differential beam path system, amplified light from a light source is input into an interferometer with a portion of light directed to a sample and the other portion directed to a reference surface. A distal end of an optical fiber is interfaced with a catheter for interrogation of the target tissue during a catheterization procedure. The reflected light from the tissue is recombined with the signal from the reference surface forming interference fringes (measured by a photovoltaic detector) allowing precise depth-resolved imaging of the target tissue on a micron scale. Exemplary differential beam path interferometers are Mach-Zehnder interferometers and Michelson interferometers. Differential beam path interferometers are further described for example in U.S. Pat. No. 7,783,337; U.S. Pat. No. 6,134,003; and U.S. Pat. No. 6,421,164, the contents of each of which are incorporated by reference herein in its entirety.

For intravascular imaging by OCT, a light beam is delivered to the vessel lumen via a fiber-optic based imaging catheter 112. The imaging catheter is connected through hardware to software on a host workstation. The hardware includes an imagining engine and PIM 105 that provides user controls. Catheter 112 is connected to PIM 105 in a similar fashion as for IVUS.

Typical intravascular OCT involves introducing the imaging catheter into a patient's target vessel using standard interventional techniques and tools such as a guide wire, guide catheter, and angiography system. Light for image capture originates within a light source and is split between an OCT interferometer and an auxiliary, or "clock", interferometer. Light directed to the OCT interferometer is further split by a splitter and recombined by splitter with an asymmetric split ratio. The majority of the light is guided into the sample path and the remainder into a reference path. The sample path includes optical fibers running through the PIM 105 and the imaging catheter 112 and terminating at imaging tip 114.

As for IVUS, OCT requires electrical signals to be communicated across a junction between catheter 112 and PIM 105. Accordingly, the connection structures discussed herein (e.g., as depicted in FIGS. 2 and 3) are applicable in OCT systems. As shown in FIGS. 2 and 3, PIM 105 provides a male connector 111 and a corresponding female connector is provided by connection member 141 of proximal end 137 of catheter 112.

Figure 4:
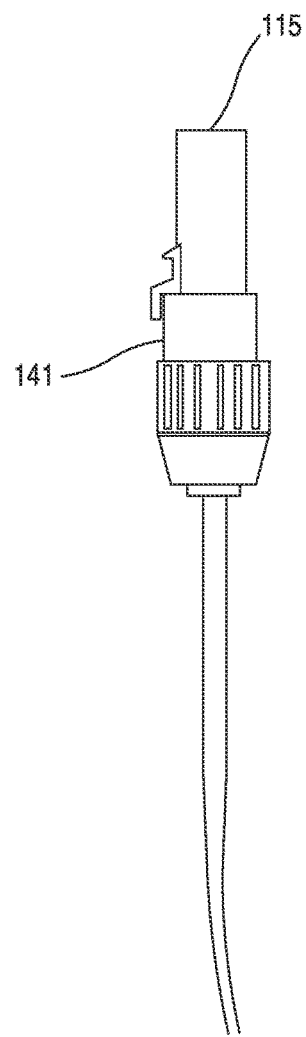
FIG. 4 gives a detailed view of a proximal end of a catheter.

FIG. 4 shows connection member 141 more closely, showing a detent mechanism that can be included so that catheter 112 clicks into place in PIM 105 and resists being pulled out. Within connection member 141 is a female connector recess 115.

Figure 5:
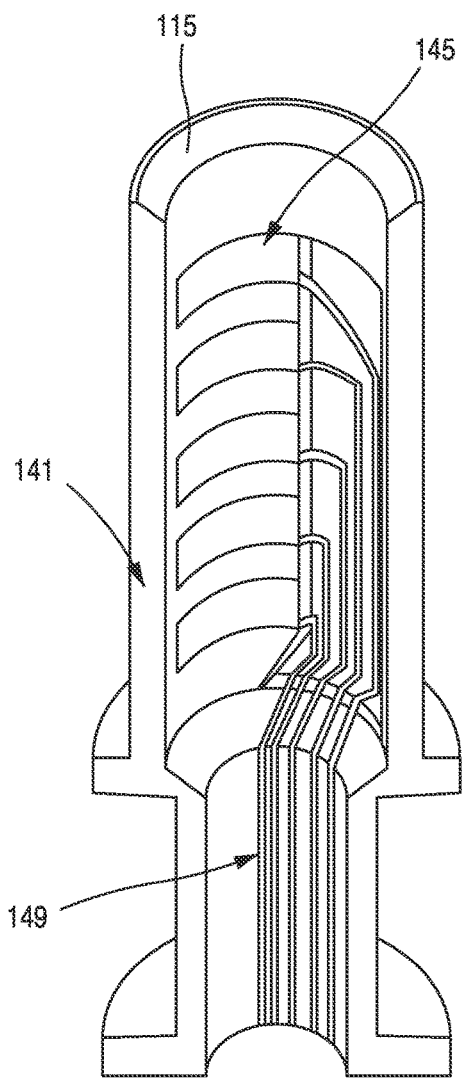
FIG. 5 shows a cutaway view of a female part of a catheter connection.

FIG. 5 shows a cutaway view showing female connector recess 115. Recess 115 includes generally cylindrical hollow defining an inward-facing surface. Connection member 141 includes a plurality of conductive contacts 145 disposed on the surface of recess 115. Each connection member is in constant electrical contact with a conductive lead 149 extending along a length of catheter body 135. Each of these contacts and leads are preferably less than about 10 μm thick. Additionally, these leads can be provided with widths that are about 100 μm or less. The contacts 145 and leads 149 may also be spaced apart by less than about 100 μm.

Figure 6:
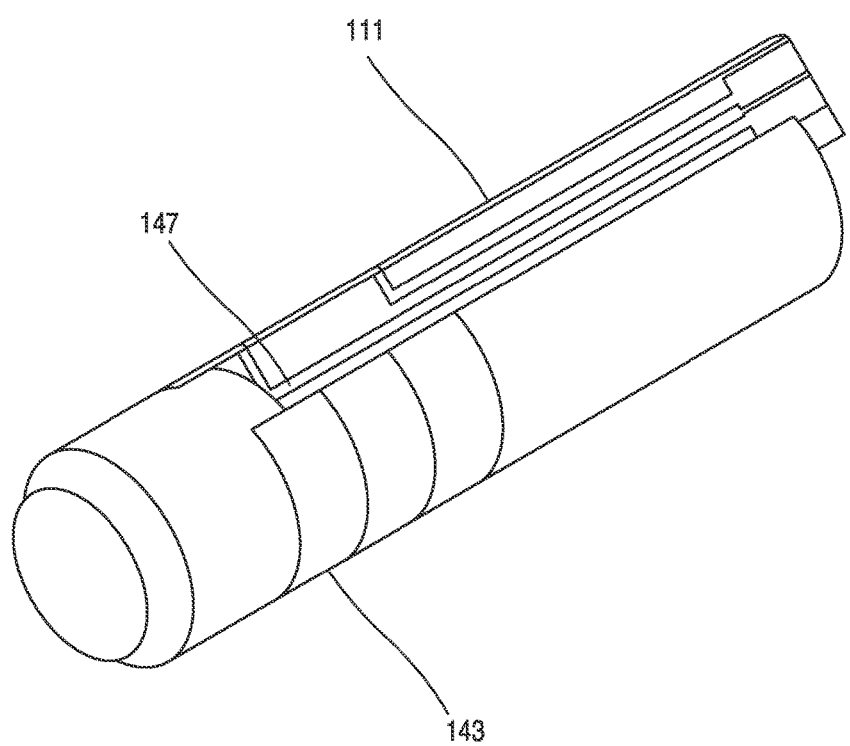
FIG. 6 displays a male component for a catheter connection.

FIG. 6 displays a male component 111 that can be manufactured according to methods described herein. Component 111 has a generally extended body of doped thermoplastic and includes contacts 143, each connected to a lead 147 to provide for the carrying of electrical signals from an imaging catheter 112 to a imaging system computer 120. Due to the improved quality of the male component 111 provided as shown in FIG. 6, imaging operations such as IVUS operations will proceed with greater success, due to fewer failures of multi-part prior art components.

Figure 7:
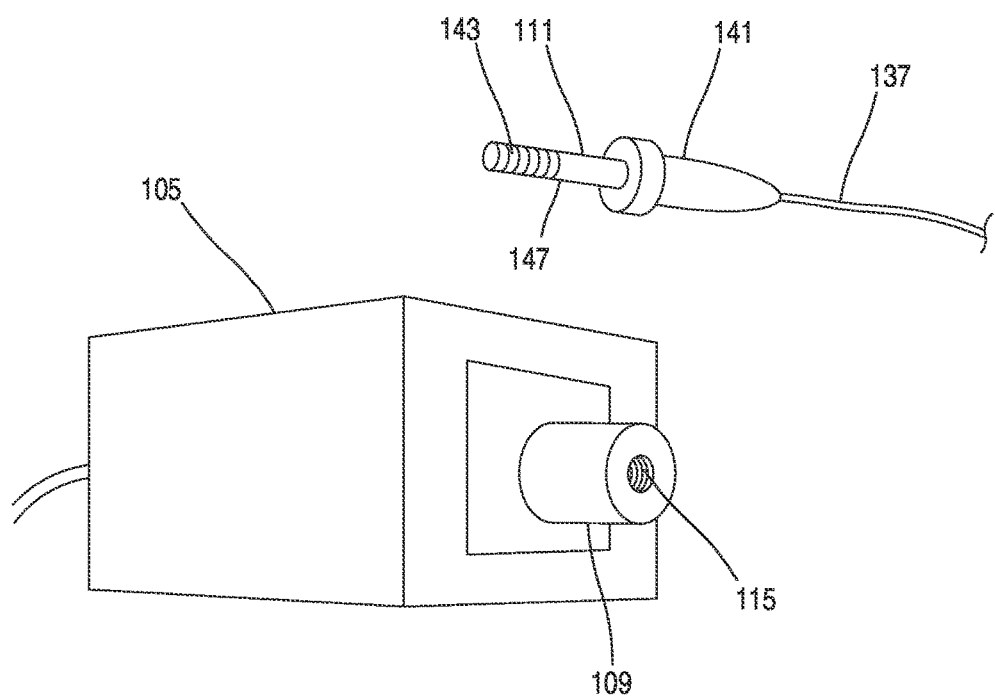
FIG. 7 is an illustration of a catheter connector and an interface module.

FIG. 7 depicts an embodiment in which male component 111 is on catheter 112, and PIM 105 provides a female connection component 115. The catheter as depicted in FIG. 7 may actually have the appearances of the catheter depicted in FIG. 3, with male component 111 shrouded by the outside housing. However, FIG. 7 does not include the housing in this depiction so that the male component 111 may be more easily visualized and understood. Connector 141 on proximal portion 137 of catheter 112 presents male component including thin contacts 143 and thin leads 147 as described above. When inserted into female coupling of connection 109 of PIM 105, each contact 143 provides a dedicated electrical signal pathway for the system. The corresponding contacts provided within PIM 105 can be any suitable mechanism or structure including ring-shaped laser structured contacts 145 (e.g., as shown in FIG. 5). In some embodiments, connector 111 participates in a specialized joint such as a rotary joint and a female portion of the connector includes a specialized contact. Any suitable contact can be used including for example, slip rings, brushes, pogo pins, or cantilevered contacts.

Figure 8:
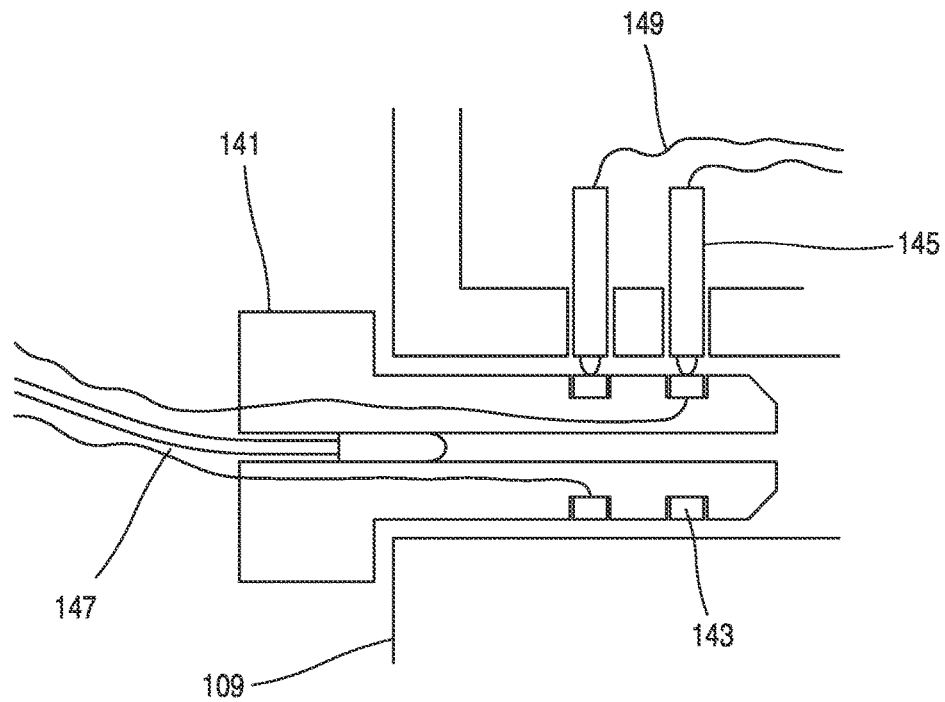
FIG. 8 is a cross-sectional view of a method for making electrical contacts.

FIG. 8 shows an embodiment in which female portion 109 includes one or more pogo pins 145 to provide electrical contacts. A portion of each pogo pion 145 is coupled to electrical lead 149. Each pogo pin 145 includes a spring that biases the tip towards contacts 143 on male connector 141.

Figure 9:
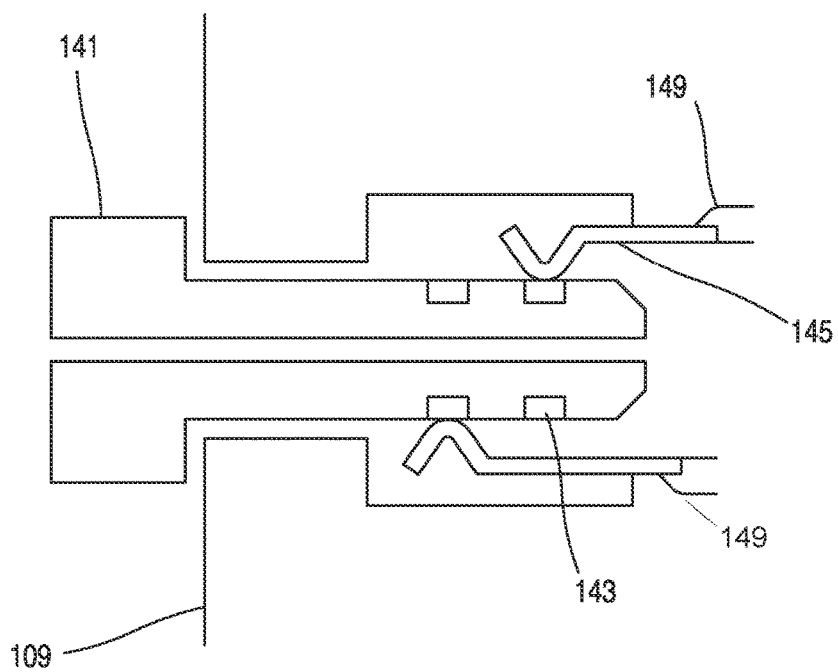
FIG. 9 illustrates an alternative method of making electrical contacts.

FIG. 9 illustrates the use of cantilevers 145 as contacts for leads 149 on the female side of the joint. Here, each cantilever 145 makes electrical contact with one contact surface 143 on the male connector. In FIG. 9, elements of catheter 112, such as a portion of body 135 and leads 149 are not depicted. The described components can be provided by any suitable fabrication method known in the art including, for example, contact printing or lithography. In certain embodiments, this arrangements of contacts and leads is provided by a process that includes molding connection member 141 from a thermoplastic material that is impregnated with a metal-organic complex. The process is based on doped thermoplastic materials on which the tracks required for the circuit layout are activated by means of targeted laser radiation, and then metallized in a chemical bath.

Figure 10:
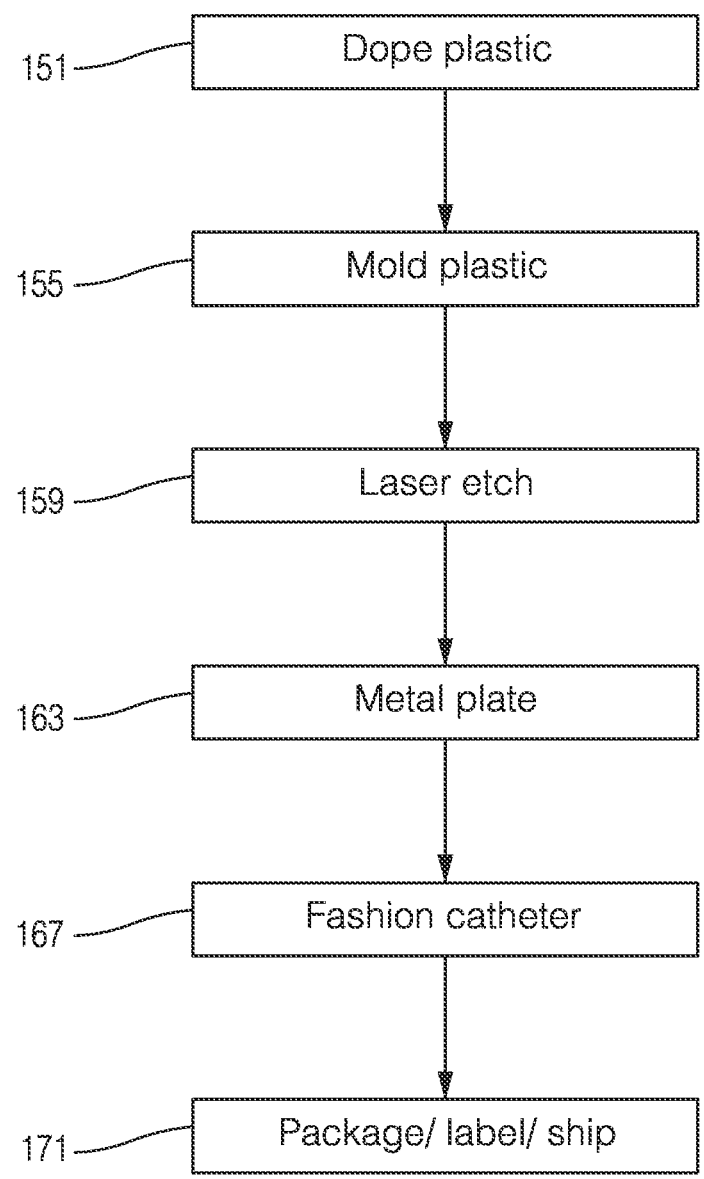
FIG. 10 is a diagram of a method of making a structured catheter connection.

FIG. 10 is a diagram of a method of making a structured catheter connection. In some embodiments, a laser-directed structuring method is employed. A suitable thermoplastic is doped 151, preferably with a chelate complex of a precious metal such as, for example, palladium or copper. The laser-directed structuring method can be employed on any thermoplastic material that can be used in a catheter. The plastic is molded 155 in a one shot molding process.

A laser is used to etch 159 the desired pattern onto the component where contacts 145 or leads 149 are desired. The laser-assisted breakdown of metal complexes creates nuclei which catalyze metal precipitation in the laser-activated zones. The laser both breaks the bonds of the metal-organic complex, making the metal available for a subsequent plating process, and also ablates the surface, providing purchase for the conductive material that will be applied during the plating process. The laser is not only able to selectively and homolytically split the metal complex, the laser beam also ablates the polymer surface. This involves absorption of the laser energy by the polymer molecules which become excited and vibrate. Ideally, the bonds between the molecules break with the input of a minimum amount of energy. In some embodiments, in addition to pure photochemical ablation, the laser beam causes relaxation and associated thermal vaporization of the material. This sublimation process may become predominant particularly when long wavelength laser light is used, e.g., an Nd:YAG laser ($\lambda$=1064 μm). After the laser tracing, contacts 145 and leads 149 are then plated on.

In certain embodiments, the plating includes an electroless plating process. This process may involve the use of chemical copper electrolytes to produce copper thicknesses of 5-8 μm. The appropriate surface finish can then be applied. Metallization is typically carried out on a rack or using a barrel plating method. The chemical plating process is used to plate 163 the component. In some embodiments, the contacts and leads adhere to the plastic body with a strength between 0.6-1.1 N/mm in accordance with DIN IEC 326. The plated component is then used in fashioning 167 imaging catheter 112, and any necessary packaging 171 is done.

With the above-described laser-directed structuring process, it is possible to produce high-resolution circuit layouts on complex three-dimensional carrier structures, such as connector pieces of medical imaging systems. The described process reduces the number of components and the assembly costs considerably. With the process, it is possible to create conductive leads 149 (instead of including wires), as well as ultra-fine circuits in the form of sensor modules or as chip housings for micro-packaging. The laser structuring simultaneously creates the surface structure at the plastic/metal boundary responsible for the high degree of adhesion.

In certain embodiments, the lasering makes use of a processing head with three optical axes. Structures smaller than 100 μm can be produced on three-dimensional moldings by the control and precision offered. The focused beam of a diode-pumped solid-state laser with a wavelength of 1064 nm is reflected with virtually no mass inertia by mirrors onto the surface of the catheter connector. An f-Theta-lens focus the beam onto the processing level, where a linear translator—a telescope with controllable lens—can shift the focal spot in a longitudinal direction by the specific defocusing of the telescope. The synchronous control of the telescope and the mirror-deflection unit guides the laser beam along complex three-dimensional surface topographies with high processing speeds of up to 4000 mm s-1.

Methods of the invention allow for structuring along any surface topography accessible by a laser beam, and the surfaces can be reached in projection. Within only a few seconds, the laser beam structures the circuit layout directly, e.g., from the computer and onto the surface of catheter part. In doing so, the laser carries out two tasks: it activates the doped LDS plastic in the areas defined by the laser as the conductor layout, and it creates a micro-rough surface which guarantees adequate adhesion for the tracks. The three-dimensional laser structuring using the described method involves focusing precisely along the surface topography of the component. In some embodiments, the method can be used to create ultra-fine structures with a width of up to 150 µm. The invention provides methods of making layers less than about 10 µm thick, e.g., between about 5 µm and about 8 µm. Thicker layers can be made, particularly where electrolytic deposition is employed. The method and process of laser-directed structuring, sometimes referred to as LPKF laser direct structuring, is described in U.S. Pat. No. 7,358,921; U.S. Pat. No. 7,060,421; U.S. Pat. No. 6,696,173; U.S. Pub. 2012/0279764; U.S. Pub. 2012/0276390; U.S. Pub. 2009/0292048; and U.S. Pub. 2004/0248439, the contents of which are incorporated by reference in their entirety for all purposes.

An additional or alternative application of the invention includes creating small-batch prototypes of new catheter connections, allowing a new medical imaging technology to be tested via prototype catheter connector parts without the costs of full production runs of parts. A prototype part can be made, for example, using an inexpensive duroplastic. The duroplastic can be made with a organo-metal substances doped in, in addition to a number of high-performance thermoplastics. The duroplasts are used as resin-hardening systems for established prototyping methods such as the vacuum casting of polyurethane resins. This allows for the creation of prototypes of catheter connections without having to invest in expensive injection molding tools.

The method can be used to very quickly manufacture electrically functional prototypes on the basis of 3-D CAD volume data. This enables the development times to be significantly shortened during the product development process. In addition, it gives users the ability to make important decisions early on for the further product development process.

In the past, products with three-dimensional structures have required complex multi-step molding processes. In the inventive method, component prototypes may be produced simply and rapidly. The ultra-fine scale of contacts 145 and leads 149 gives high degrees of flexibility for the conductor layout because modifications can be easily incorporated by changing the structuring data. This enables subsequent changes to be made to the connector design (e.g., add more channel information to WUS or OCT system) without having to modify any tools.

By modifying a polymer in a suitable way with non-ablatable or only poorly ablatable fillers (mostly inorganic materials), lasering results in microscopically-small cavities and undercuts which in themselves enable good adhesion between the plastic and the precipitating metal layer without the need for complicated extra treatment. One of the main advantages of processing materials with laser light is the feedback-free impact on the material combined with high processing speeds. Circuit layout is controlled by an optical processing head and is not predetermined by the geometry of a fixed tool (e.g., stamping dyes, 2-shot-tools). This gives shorter lead times and high levels of flexibility and economic efficiency. It may be desirable to make a small batch (e.g., one or a few) of prototypes by vacuum casting of polyurethane resins. This is done on the basis of a stereolithographically produced original model used to create a silicon mold in which up to 25 polyurethane prototypes can subsequently be made by vacuum casting. As with full production run materials (thermoplastics), polyurethane is doped with a metal complex. Because polyurethane is a duroplastic resin-hardening system, only one component—preferentially the resin—is modified. The resulting vacuum-cast prototypes can then be laser-activated—in precisely the same way as thermoplastic components during series production—to allow subsequent selective metal precipitation on the laser-treated areas in the subsequent metallization process.

As used herein, the word "or" means "and or or", sometimes seen or referred to as "and/or", unless indicated otherwise.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An intravascular device, comprising:
   an elongate member having a proximal portion and a distal portion;
   a sensor positioned at the distal portion of the elongate member; and
   a connector in communication with the sensor and positioned at the proximal portion of the elongate member, the connector comprising:
   an extended body having a proximal end and a distal end, wherein the extended body comprises a thermoplastic doped with an organo-metal complex;
   a conductive contact disposed on a surface of the doped thermoplastic of the proximal end; and
   a conductive trace extending along a length of the surface of the doped thermoplastic of the body and in electrical contact with the conductive contact.

2. The intravascular device of claim 1, wherein the conductive contact of the connector is less than about 10 µm thick.

3. The intravascular device of claim 1, wherein the conductive trace comprises a metal trace less than about 150 µm wide and less than about 10 µm thick.

4. The intravascular device of claim 1, wherein the conductive contact of the connector is on an outer surface of the proximal end.

5. The intravascular device of claim 1, wherein the conductive contact of the connector is on an inner surface of the proximal end.

6. The intravascular device of claim 1, wherein the connector further comprises a plurality of conductive contacts disposed on the surface of the doped thermoplastic of the proximal end and each in electrical contact with one of a plurality of conductive traces extending along the length of the surface of the doped thermoplastic of the body.

7. The intravascular device of claim 6, wherein the proximal end of the connector defines a male form factor plug configured so that if inserted into a corresponding jack the plug may be rotated with respect to the jack while maintaining constant electrical contact from each of the conductive contacts to corresponding conductive contacts of the jack.

8. The intravascular device of claim 1, wherein the connector further comprises a plurality of conductive traces extending along the length of the body, wherein each of the plurality of conductive traces is less than about 150 μm wide and less than about 10 μm thick, and further wherein the plurality of conductive traces are spaced apart by less than about 200 μm.

9. The intravascular device of claim 8, wherein each of plurality of conductive traces of the connector are less than about 110 μm wide and less than about 8 μm thick, and further wherein the plurality of conductive traces are spaced apart by less than about 160 μm.

10. The intravascular device of claim 1, wherein the conductive contact of the connector is less than about 5 μm thick and the conductive trace is less than about 5 μm thick.

11. The intravascular device of claim 10, wherein the conductive contact of the connector is less than about 3 μm thick and the conductive trace is less than about 3 μm thick.

12. The intravascular device of claim 1, wherein the body of the connector is formed of a unitary piece of the doped thermoplastic.

13. The intravascular device of claim 1, wherein the conductive contact and the conductive trace of the connector are laser patterned.

14. The intravascular of claim 1, wherein the doped thermoplastic of the connector consists of a thermoplastic doped with at least one of palladium or copper.

15. The intravascular device of claim 14, wherein at least one of the conductive contact or the conductive trace of the connector is formed of copper having a thickness between 5 μm and 8 μm.

16. An intravascular device, comprising:
an elongate member having a proximal portion and a distal portion;
a sensor positioned at the distal portion of the elongate member; and
a connector in communication with the sensor and positioned at the proximal portion of the elongate member, the connector comprising:
a unitary body formed of an organo-metal doped thermoplastic, the unitary body having a proximal end;
a plurality of conductive contacts formed on a laser-patterned surface of the organo-metal doped thermoplastic of the proximal end; and
a plurality of conductive traces extending distally from respective ones of the plurality of conductive contacts along the laser-patterned surface of the organo-metal doped thermoplastic.

17. The intravascular device of claim 16, wherein the laser-patterned surface of the connector is an outer surface of the unitary body.

18. The intravascular device of claim 16, wherein the laser-patterned surface of the connector is an inner surface of the unitary body.

19. The intravascular device of claim 16, wherein the connector further comprises a detent mechanism coupled to the unitary body, the detent mechanism configured to physically engage a patient interface module (PIM) to secure the connector to the PIM.

20. A system, comprising:
an intravascular device, comprising:
a sensor positioned at a distal portion of an elongate member; and
a connector in communication with the sensor and positioned at a proximal portion of the elongate member, the connector comprising:
an extended body having a proximal end and a distal end, wherein the extended body comprises a thermoplastic doped with an organo-metal complex;
a conductive contact disposed on a surface of the doped thermoplastic of the proximal end; and
a conductive trace extending along a length of the surface of the doped thermoplastic of the body and in electrical contact with the conductive contact; and
a patient interface module (PIM) coupled to the intravascular device via the connector.

* * * * *